(12) United States Patent
Takeishi et al.

(10) Patent No.: US 8,276,452 B2
(45) Date of Patent: *Oct. 2, 2012

(54) ULTRASONIC INSPECTION APPARATUS

(75) Inventors: Masayuki Takeishi, Hyogo (JP);
Masanori Shimazaki, Hyogo (JP);
Masahiro Yui, Hyogo (JP); Tomoyuki Hirayama, Hyogo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 463 days.

This patent is subject to a terminal disclaimer.

(21) Appl. No.: 12/517,234

(22) PCT Filed: Jan. 24, 2008

(86) PCT No.: PCT/JP2008/050973
§ 371 (c)(1),
(2), (4) Date: Jun. 2, 2009

(87) PCT Pub. No.: WO2008/126437
PCT Pub. Date: Oct. 23, 2008

(65) Prior Publication Data
US 2010/0058871 A1 Mar. 11, 2010

(30) Foreign Application Priority Data
Mar. 30, 2007 (JP) .................. 2007-092515

(51) Int. Cl.
*G01B 17/02* (2006.01)
(52) U.S. Cl. .......................... 73/627; 73/596
(58) Field of Classification Search .................. 73/596, 73/627
See application file for complete search history.

(56) References Cited

U.S. PATENT DOCUMENTS

| 4,137,991 A | | 2/1979 | Melcher et al. |
| 5,457,997 A | * | 10/1995 | Naruo et al. ................. 73/643 |
| 6,181,431 B1 | * | 1/2001 | Siu ............................. 356/502 |

(Continued)

FOREIGN PATENT DOCUMENTS
EP 1152240 A2 7/2001
(Continued)

OTHER PUBLICATIONS
International Search Report of PCT/JP2008/050973, Mailing Date of Apr. 15, 2008.
(Continued)

*Primary Examiner* — Max Noori
(74) *Attorney, Agent, or Firm* — Westerman, Hattori, Daniels & Adrian, LLP (57) ABSTRACT

An ultrasonic inspection apparatus is provided in which the size of the apparatus can be made compact by using laser light, the degradation and deformation of the inspected object is prevented, and a broad range of inspections can be carried out. An ultrasonic inspection apparatus (1) is provided with a laser apparatus (5) that irradiates laser light and a volumetric inspection ultrasonic wave transmitter (17) having a transmitting diaphragm (39) that is irradiated by the laser light emitted by the laser apparatus (5) and that generates ultrasonic waves (C); and the ultrasonic inspection apparatus (1) carries out volumetric inspections by irradiating the ultrasonic waves (C) that are generated by the transmitting diaphragm (39) of the ultrasonic wave transmitting portion (17) to the inspected object. In addition, the ultrasonic inspection apparatus (1) is further provided with a surface inspection ultrasonic wave transmitting portion (19), and enables the carrying out of inspections having the characteristics of volumetric inspections and surface inspections, that is, hybrid inspections.

4 Claims, 5 Drawing Sheets

U.S. PATENT DOCUMENTS

| | | | |
|---|---|---|---|
| 6,490,047 B2 * | 12/2002 | Siu | 356/502 |
| 6,632,178 B1 | 10/2003 | Fraser | |
| 7,421,900 B2 * | 9/2008 | Karasawa et al. | 73/621 |
| 7,463,363 B2 * | 12/2008 | Drake et al. | 356/502 |
| 2001/0039836 A1 | 11/2001 | Ogawa | |
| 2010/0206082 A1 * | 8/2010 | Shimazaki et al. | 73/627 |

FOREIGN PATENT DOCUMENTS

| | | |
|---|---|---|
| JP | 58-11639 B2 | 3/1983 |
| JP | 7-306188 A | 11/1995 |
| JP | 10-288607 A | 10/1998 |
| JP | 11-326580 A | 11/1999 |
| JP | 2984390 B2 | 11/1999 |
| JP | 2000-28589 A | 1/2000 |
| JP | 2002-17723 A | 1/2002 |
| JP | 2002-328116 A | 11/2002 |
| JP | 2005-43139 A | 2/2005 |
| JP | 2005-175919 A | 6/2005 |
| JP | 2005-253751 A | 9/2005 |
| RU | 1793364 A1 | 2/1993 |
| RU | 1804837 A1 | 3/1993 |
| SU | 853524 A1 | 8/1981 |

OTHER PUBLICATIONS

Biagi. E et al.; "Fully Fiber Optic Ultrasonic Probes for Virtual Biopsy"; 2006 IEEE Ultrasonics Symposium, pp. 556-559.

Chinese Office Action dated Mar. 30, 2011, issued in corresponding Chinese Patent Application No. 200880001377.1.

Russian Office Action dated Aug. 20, 2010, issued in corresponding Russian Patent Application No. 2009122649.

Foreign Associate letter dated Sep. 20, 2010, summarizing Russian Office Action dated Aug. 20, 2010.

International Search Report of PCT/JP2008/064326, mailing date of Nov. 11, 2008.

Soviet Union Office Action dated Oct. 27, 2010, issued in corresponding Soviet Union Patent Application No. 2010102123/28(002973).

Decision of Russian Patent Grant dated Feb. 17, 2011, issued in corresponding Russian Patent Application No. 2010102123.

United States Office Action dated Jun. 18, 2012, issued in related U.S. Appl. No. 12/670,788.

* cited by examiner

ULTRASONIC INSPECTION APPARATUS

TECHNICAL FIELD

The present invention relates to an ultrasonic inspection apparatus.

BACKGROUND ART

Inspection apparatuses that use ultrasonic waves have been practically applied, for example, to non-destructive examinations in medicine and inspections in nuclear power plants. Because ultrasonic defect inspections can relatively easily detect, for example, defects in the interior of a material, it plays a significant role in the inspection of critical parts of structural materials. In an ultrasonic defect inspection, a voltage element such as that disclosed in Patent Document 1 is used, for example, in the transmission of ultrasonic waves.

This voltage element has a comparatively large radius of, for example, about 20 mm, and thus, the size of the apparatus is increased. Therefore, the measurement of narrow spaces and parts having a complicated shape is difficult. In addition, because the frequency band of the ultrasonic waves is limited by the particular frequency of the voltage element, there is a problem in that, for example, it is not very suitable for uses such as the image display of a member surface.

A laser ultrasonic wave method that is disclosed, for example, in Patent Document 2, has been proposed as a means for solving these problems.

This invention uses an optical fiber to irradiate laser light to an inspected object, an ultrasonic wave is generated on the surface of the inspected object by this laser light, and the ultrasonic wave that is propagated through the inspected object is detected by using the received laser light. Defects are detected by sensing the changes in these ultrasonic waves, and the depth can be identified by performing a frequency analysis of the received ultrasonic waves.

In particular, because a fine light fiber is used in the ultrasonic wave generation, the size of the apparatus can be reduced, and the apparatus can be used in the measurement of narrow spaces and for members having a complicated shape.

Patent Document 1: Japanese Unexamined Patent Application, First Publication No. 2000-28589

Patent Document 2: Japanese Unexamined Patent Application, First Publication No. 2005-43139

DISCLOSURE OF THE INVENTION

The invention that is disclosed in Patent Document 2 directly irradiates the laser light to the inspected object, and thus, there is a problem in that the inspected object may deteriorate or deform.

Because of this, there are problems in that the intensity of the laser light is limited and thus an adequate examination cannot be carried out, and the range of the inspected objects, which are the object of inspection, is restricted.

Furthermore, there is a problem in that it is not possible to inspect locations through which laser light cannot pass. An example of such a location is one where sodium, which is the coolant of a fast breeder reactor, is present.

In consideration of the above circumstances, it is an object of the present invention to provide an ultrasonic inspection apparatus that uses a laser light, reduces the size of the apparatus, prevents the deterioration and deformation of the inspected object, and enables the carrying out of advantageous inspections over a wide range.

The present invention uses the following means in order to solve the problems described above.

One aspect of the present invention provides an ultrasonic inspection apparatus that includes a laser apparatus that irradiates laser light and an ultrasonic wave transmitting portion having a first diaphragm that is irradiated by the laser light emitted by the laser apparatus and that generates ultrasonic waves, and the ultrasonic inspection apparatus carries out inspections by irradiating the ultrasonic waves that are generated by the first diaphragm of the ultrasonic wave transmitting portion to the inspected object.

According to the present aspect, the first diaphragm generates ultrasonic waves due to the laser light generated by the laser apparatus irradiating to the first diaphragm, and these ultrasonic waves are irradiated to the inspected object. Thus, thus it is possible to prevent the deterioration and the deformation of the inspected object.

Thereby, the intensity of the generated ultrasonic waves can be increased because high-output laser light can be handled. Thus, advantageous inspections can be carried out. In addition, because sufficient inspections can be carried out even if the distance to the inspected object large, the angle of the beam spread can be increased. Thereby, because a high resolution can be used, the inspecting precision can be increased.

In this case, preferably, the output of the laser light is controlled so as to remain within a viable range, which is a range in which the first diaphragm is not degraded or damaged by the laser light.

Furthermore, the ultrasonic inspection apparatus can be made compact because the size of the ultrasonic wave transmission portion can be reduced by using an optical fiber for the transmission of the laser light.

In addition, ultrasonic waves are used in the inspections, and thus, it is possible to inspect locations through which the laser light cannot pass. An example of such a location is one in which sodium, which is the coolant for a fast breeder reactor, is present.

In addition, in the aspect described above, it is advantageous that an intensity adjusting means, which adjusts the intensity of the laser light incident to the first diaphragm, is provided in the laser apparatus.

Thereby, because the intensity of the laser light that is irradiated to the first diaphragm by the intensity adjusting means can be adjusted, the intensity and the frequency of the ultrasonic waves that are generated by the first diaphragm can be adjusted.

Thereby, because optimal ultrasonic waves that are compatible with the type of the inspected object and the inspection locations can be generated, it is possible to improve the inspection precision and the inspection efficiency and the like.

Note that examples of an intensity adjusting means include a means that adjusts the output of the laser apparatus, a means that adjusts the pulse width of the laser light, and a means that adjusts the spot diameter of laser light that is incident to the first diameter, such as a filter, for example, an ND filter (Neutral Density Filter), that adjusts the amount of laser light, or a condensing lens or the like.

In addition, in the aspect described above, it is advantageous that the first diaphragm be one that has prescribed frequency characteristics.

Thereby, by using an ultrasonic inspection apparatus provided with an optimal ultrasonic transmitting portion that is compatible with both the type of the inspected object and the type of the inspection, the inspection precision and the inspection efficiency and the like can be improved.

Moreover, the first diaphragm may be formed by a single material, may be clad plate that includes a plurality of laminated materials, or may be a complex material in which a plurality of materials are combined.

In addition, in the aspect described above, it is advantageous that the first diaphragm be one that has a favorable laser light absorption efficiency.

Thereby, because the majority of the energy of the laser light is transferred to the first diaphragm, the energy efficiency can be improved.

In addition, in the aspect described above, it is advantageous that a coating be applied at least to the first diaphragm at the surface to which the laser light is irradiated.

Thereby, because the coating suppresses deterioration of and damage to the first diaphragm that is caused by the laser light, the intensity of the laser light can be increased, and the intensity of the generated ultrasonic waves can thereby be increased.

In addition, for example, when coated with a coating material having a favorable laser light absorption efficiency, a majority of the energy of the laser light is transferred to the first diaphragm, and it is thereby possible to improve the energy efficiency.

In addition, in the aspect described above, it is advantageous that the ultrasonic wave transmitting portion be provided with a plurality of devices that generate ultrasonic waves having different frequencies.

Thereby, one ultrasonic inspection apparatus can handle changes in the inspected object type and the inspection location and the like.

In addition, for example, inspections having different characteristics such as a volumetric inspection and a surface inspection, that is, hybrid inspection, can be carried out.

In addition, in the aspect described above, it is advantageous to provide an ultrasonic wave receiving portion that includes a second diaphragm and a laser member, where the second diaphragm vibrates due to receiving the ultrasonic waves that have been reflected from the inspected object and the laser member emits a laser light to the second diaphragm and receives laser light that has been reflected from the second diaphragm. The ultrasonic wave receiving portion is integrally supported with the ultrasonic wave receiving portion.

In this manner, because independently setting the positions of the ultrasonic wave transmitting portion and the ultrasonic wave receiving portion becomes unnecessary, inspections can be carried out efficiently.

According to the present invention, because the first diaphragm generates ultrasonic waves due laser light that is emitted from the laser apparatus being irradiated to the first diaphragm, and the ultrasonic waves are irradiated to the inspected object, it is possible to prevent the deterioration and deformation of the inspected object.

Thereby, advantageous inspections can be carried out, and the size of the ultrasonic inspection apparatus can be reduced.

EXPLANATION OF REFERENCE

1: ultrasonic inspection apparatus
5: laser apparatus
17: volumetric inspection ultrasonic wave transmitter
19: surface inspection ultrasonic wave transmitter
21: ultrasonic wave receiver
33: ND filter
35: condensing lens
39: transmitting diaphragm
51: receiving diagram
53: structural member

BEST MODE FOR CARRYING OUT THE INVENTION

Below, the ultrasonic inspection apparatus 1 according to an embodiment of the present invention will be explained based on FIG. 1 to FIG. 5. The ultrasonic inspection apparatus 1 carries out ultrasonic wave defect detection on a member in salt, which is the cooling material for fast breeder reactors. Thus, the inspection apparatus 1 carries out volumetric inspection, by which the condition of the interior is inspected, and surface inspection, by which the condition of the surface is inspected.

Figure 1:
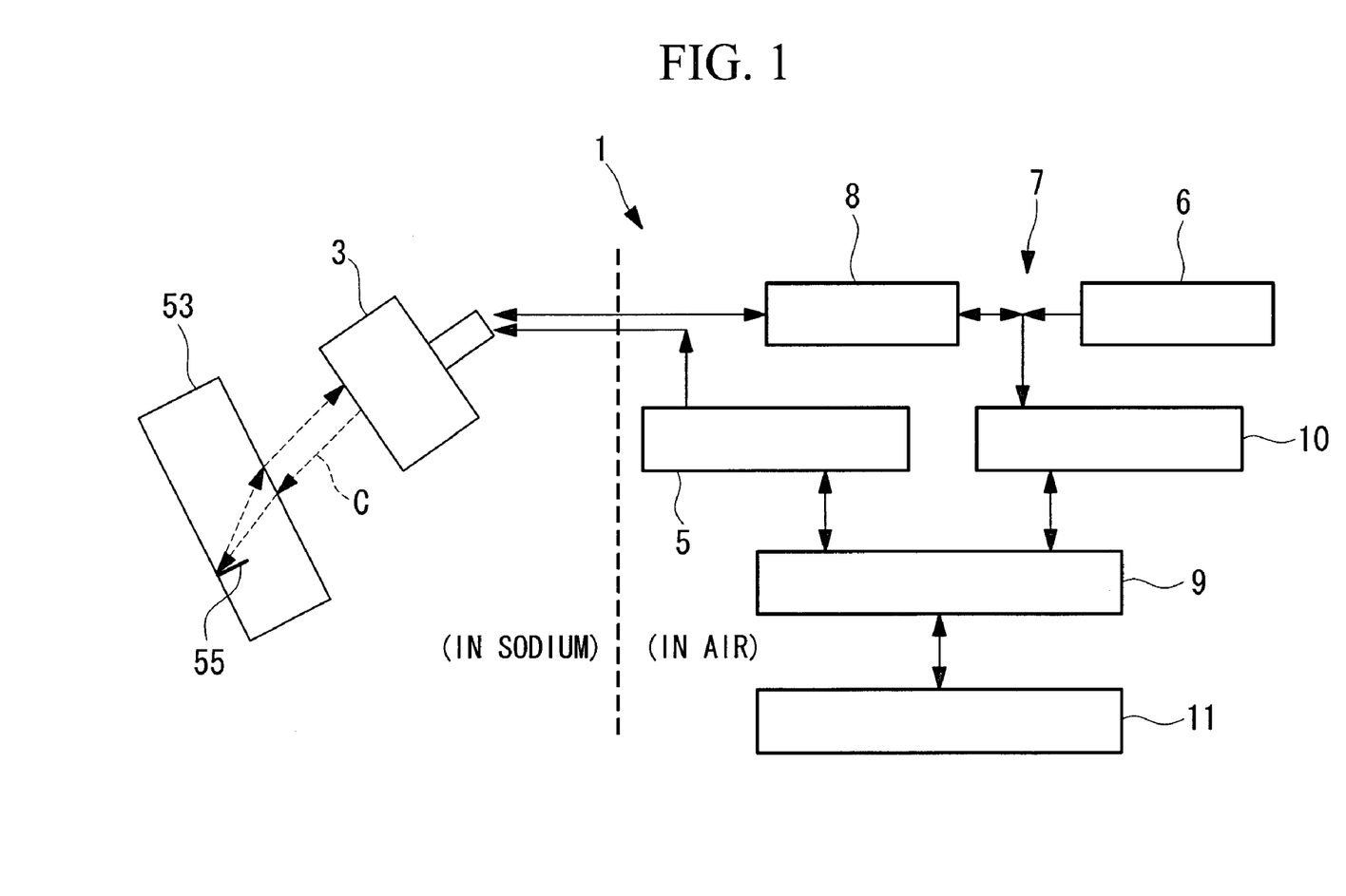
FIG. 1 is a block diagram that shows the overall schematic structure of the ultrasonic inspection apparatus according to an embodiment of the present invention.

FIG. 1 is a block diagram that shows the overall schematic structure of the ultrasonic inspection apparatus 1.

The ultrasonic inspection apparatus 1 is provided with a probe 3 that transmits and receives ultrasonic waves; a laser apparatus 5 that emits laser light; a laser-receiving portion 7 that receives and transmits laser light for ultrasonic wave reception; a data collecting apparatus 9 that stores the transmitted and received data and directs the operation of the laser apparatus 5 and the laser-receiving apparatus 7; and a data processing and display apparatus 11 that processes and displays the transmitted and received data.

The laser-receiving portion 7 is provided with a laser oscillator 6 that generates a laser light; a light switch 8 that emits laser light to and receives laser light from an optical fiber; and a laser interferometer 10 that causes interference between the transmitted laser light and the received laser light.

Figure 2:
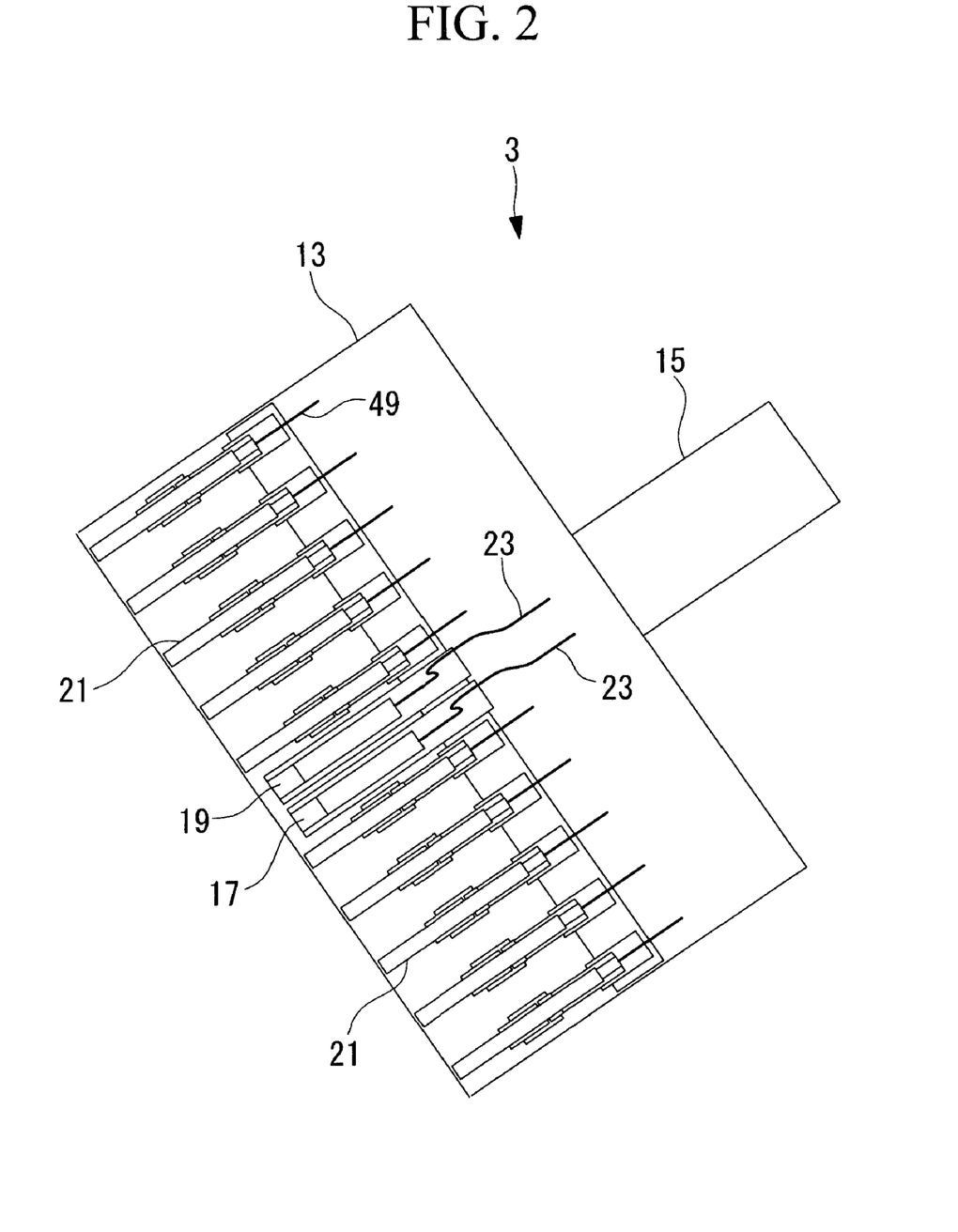
FIG. 2 is a cross-sectional view that shows the schematic structure of the probe according to an embodiment of the present invention.

FIG. 2 is a cross-sectional diagram that shows a schematic structure of the probe 3.

The probe 3 is provided with a main body 13, which is a box that has a substantially rectangular solid shape; a passage portion 15 having a cylindrical shape that is mounted at the substantially center portion of one surface of the main body 13 and through which an optical fiber is passed; a volumetric inspection ultrasonic wave transmitting portion (ultrasonic wave transmitting portion) 17 that is mounted at the inner portion of the main body 13; a surface inspection ultrasonic wave transmitting portion (ultrasonic wave transmitting portion) 19; and a plurality of ultrasonic wave receiving portions 21.

The volumetric inspection ultrasonic wave transmitting portion 17, the surface inspection ultrasonic wave transmitting portion 19, and the ultrasonic wave receiving portions 21 have a substantially cylindrical shape, and they are mounted on the side of the main body 13 that is away from the passage portion 15 so that the axis thereof lies in a direction that intersects the surface on which the passage portion 15 of the main body 13 is mounted.

The plurality of ultrasonic wave receiving portions 21 are arranged in a matrix (for example, a 10 row by 10 column matrix) at substantially equal intervals.

The volumetric inspection ultrasound transmitting portion 17 and the surface inspection ultrasonic wave transmitting portion 19 are arranged at the substantial center of a group of ultrasonic wave receiving portions 21.

Figure 3:
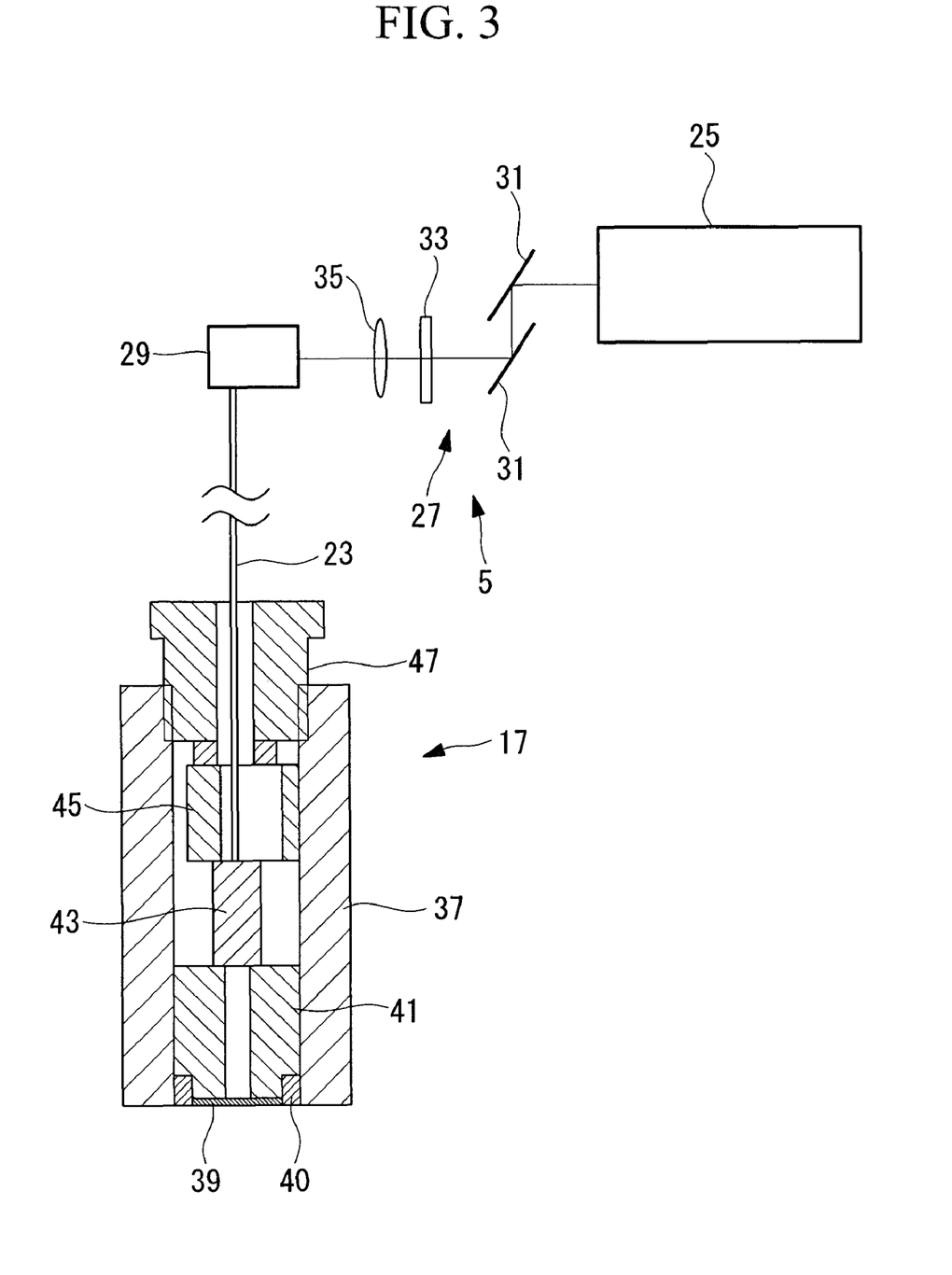
FIG. 3 is a block diagram that shows the schematic structure of the ultrasonic wave transmission system according to an embodiment of the present invention.

The volumetric inspection ultrasonic wave transmitting portion 17 and the surface inspection ultrasonic wave transmitting portion 19 are linked to the laser apparatus 5 by optical fibers 23 (FIG. 2 and FIG. 3).

Because the volumetric inspection ultrasonic wave transmitting portion 17 and the surface inspection ultrasonic wave transmitting portion 19 have substantially identical structures, the volumetric inspection ultrasonic wave transmitting portion 17 will be explained.

The laser apparatus 5 is provided with a laser oscillator 25, a laser light path 27, and a feed portion 29 that feeds laser light to an optical fiber, and is formed by, for example, an optical switch and the like. The laser light path 27 is provided with a pair of mirrors 31, an ND filter 33, and a condensing lens 35.

Plural ND filters 33 is provided such that they can be switched, and the amount of laser light is adjusted by switching these filters.

The condensing lens 35 can be moved along the laser light path 27, and the diameter (the diameter of the laser light that is incident on the transmitting diaphragm (the first diaphragm) 39 described below) of the laser light that is incident to the optical fiber 23 can thereby be adjusted.

The volumetric inspection ultrasonic wave transmitter 17 is provided with a hollow substantially cylindrical main body 37; a transmitting diaphragm 39 that is mounted at one end portion of the main body 37; a heat resistant damper 40; a backup ring 41 that is arranged at the other end side of the transmitting diaphragm 39 and supports the same; a ferrule 43, which is a linking member that arranges the optical fibers 23 that are disposed at the other end side of the backup ring 41 in a prescribed positional relationship; an eccentric hole ring 45 that is arranged at the other end side of the ferrule 43 and presses the ferrule; and a tap screw 47 that is threaded into the hollow portion of the other end portion of the main body 37 and restrains the member that is arranged at the one end side.

The volumetric inspection ultrasonic wave transmitter 17 and the surface inspection ultrasonic wave transmitter 19 are arranged such that the transmitting diaphragm 39 faces the surface that is opposed to the passage portion 15 of the main body 13.

The transmitting diaphragm 39 is, for example, made of stainless steel, has a diameter of 4 mm, and a thickness of 30 to 50 μm.

The transmitting diaphragm 39 made of any suitable material and having any suitable dimensions (thickness and the like) can be used. In addition, the transmitting diaphragm 39 may be formed by a single material, may be a clad plate in which a plurality of materials are laminated, or may be a complex material in which plural materials are combined.

The material and dimensions of the transmitting diaphragm 39 are selected by taking into consideration the intensity of the laser light from the laser apparatus 5, and the intensity and frequency characteristics of the ultrasonic waves generated thereby. In addition, the transmitting diaphragm 39 is preferably made of a material that has a high laser light absorption efficiency in order to increase the energy efficiency.

In addition, the transmitting diaphragm 39 may have a coating applied to the surface to suppress deterioration and damage.

A quartz glass, sapphire, and silica or the like, which are optical materials that pass laser light and have a good wavelength penetration, are preferable for use as a coating material because they improve the energy efficiency.

In addition, for example, applying an iron or aluminum oxide film may be considered. These oxide films can improve the absorption rate of the laser light and can suppress deterioration and damage.

Figure 4:
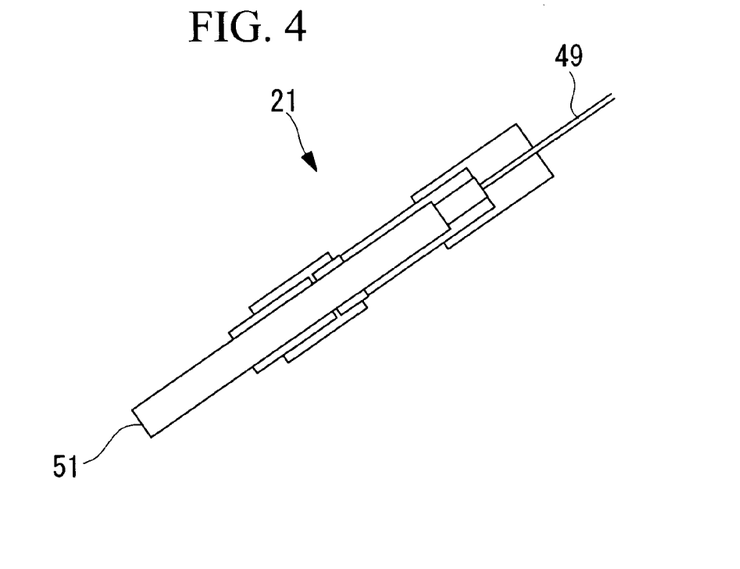
FIG. 4 is a cross-sectional view that shows the schematic structure of the ultrasonic wave receiving portion according to an embodiment of the present invention.

FIG. 4 is a cross-sectional view that shows the schematic structure of a ultrasonic wave receiving portion 21.

Each ultrasonic wave receiving portion 21 has a substantially cylindrical shape and an optical fiber 49, which connects to the optical switch 8, is connected to one end side thereof. A receiving diaphragm (second diaphragm) 51 is installed at the other end portion of each ultrasonic wave receiving portion 21.

The ultrasonic wave receiving portions 21 are arranged such that the receiving diaphragm 51 faces the surface that is opposite to the passage portion 15 of the main body 13.

The operation of the ultrasonic inspection apparatus 1 according to the embodiment that has been explained above will now be explained.

The probe 3 is disposed opposite to the structural member (inspected object) 53 that is the object of inspection. When carrying out volumetric inspection, which inspects for damage 55 at the interior of the structural member 53, the volumetric inspection ultrasonic wave transmitting portion 17 is used.

When the laser oscillator 25 generates the laser light, the laser light is incident to the feed portion 29 after passing through the laser light path 27. At the feed portion 29, the laser light is converted to a shape that can pass through the optical fiber 23 on the volumetric inspection ultrasonic wave transmitting portion 17 side. This converted laser light passes through the optical fiber 23 and irradiates the transmitting diaphragm 39 from the ferrule 43.

When the laser light is irradiated to the transmitting diaphragm 39, the transmitting diaphragm 39 generates ultrasonic waves.

Figure 5:
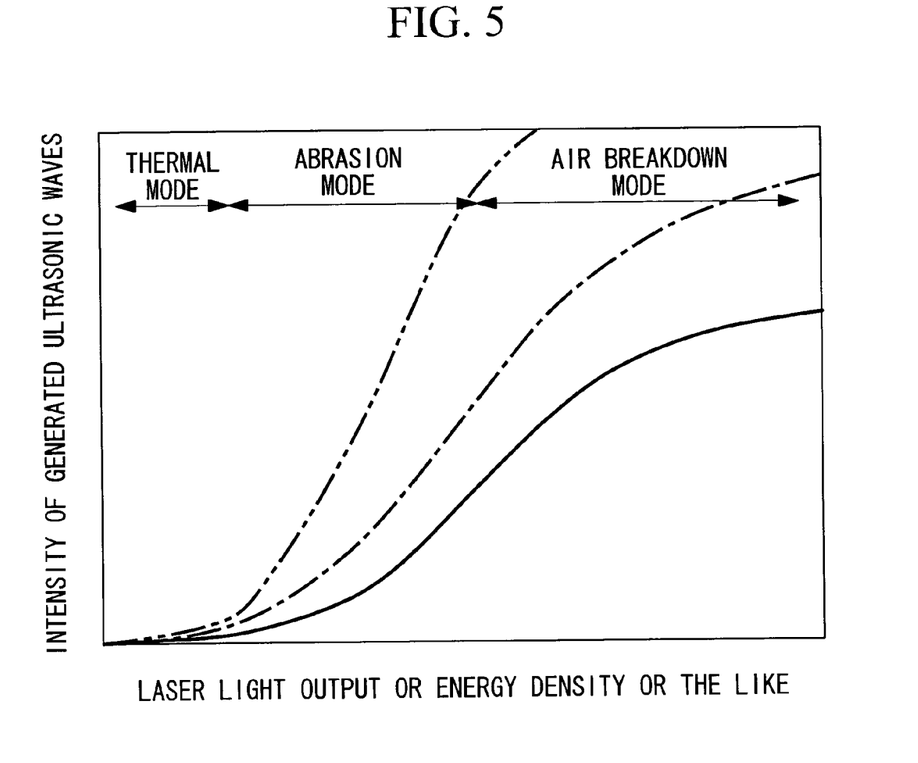
FIG. 5 is a graph that shows the relationship between the laser intensity and the intensity of the generated ultrasonic waves.

At this time, the intensity of the generated ultrasonic waves changes in response to the laser light output or the energy density of the laser light, as shown by the solid line in FIG. 5.

Where the laser light output or the energy density of the laser light or the like is small, the energy of the laser light is used to raise the temperature, and the intensity of the generated ultrasonic waves is small. This part is referred to as the "thermal mode".

When the laser light output or the energy density of the laser light or the like is large, the intensity of the generated ultrasonic waves rapidly increases. At this stage, the transmitting diaphragm 39 is corroded by the laser light, and thus, this is referred to as the "abrasion mode".

When the laser light output or the energy density of the laser light or the like becomes even larger, the corrosion action on the transmitting diaphragm 39 becomes large, and a portion thereof is vaporized. Because laser light is scattered or absorbed, the proportion of the energy that the laser light supplies to the transmitting diaphragm 39 is reduced. Consequently, the rate of increase of the intensity of the generated ultrasonic waves becomes small, and thus the energy efficiency of the laser light is reduced. This state is referred to as the "air breakdown mode".

Therefore, taking into consideration both the energy efficiency and the damage to the transmitting diaphragm 39, the intensity of the laser light (the laser light output or the energy density of the laser light or the like) is selected so as to be within the range of the abrasion mode.

When the necessary ultrasonic wave intensity cannot be obtained at the selected energy, a coating, for example, is applied to the transmitting diaphragm 39.

When, for example, the transmitting diaphragm 39 is coated by an iron or aluminum oxide film, the absorption efficiency of the laser light is increased, and thus, for example, the intensity of the generated ultrasonic waves increases, as shown by the single dashed line that is shown in FIG. 5.

In addition, for example, when the transmitting diaphragm 39 is coated by a material that readily transmits the laser light, such as quartz glass, the abrasion is suppressed, and thus, the intensity of the generated ultrasonic waves increases, as shown by the double dashed line that is shown in FIG. 5.

In addition, if this increase is still insufficient, the size and material and the like of the transmitting diaphragm 39 can be redesigned.

In this manner, the ultrasonic waves C that are generated by the transmitting diaphragm 39 of the volumetric inspection ultrasonic wave transmitting portion 17 are irradiated toward the structural member 53.

These ultrasonic waves C are adjusted such that their principal frequency is 2 to 5 MHz. In other words, requirements such as the material and the dimensions of the transmitting diaphragm 39, and intensity of the laser light of the laser apparatus 5 are set such that the principal frequency of the generated ultrasonic waves C is 2 to 5 MHz.

The ultrasonic waves C that are irradiated to the structural member 53 are reflected by the structural member 53, advance toward the probe 3, and then cause the receiving diaphragm 51 of each of the ultrasonic wave receiving portions 21 to vibrate. At this time, if there is damage 55 in the structural member 53, the direction of the ultrasonic waves C will be changed by the damage 55, and the phase of the vibration of the receiving diaphragms 51 will deviate from a prescribed state.

At this time, laser light is generated by the laser oscillator 6 of the laser-receiving portion 7, and the receiving diaphragms 51 is irradiated via the optical switch 8 and the optical fiber 49. The irradiated laser light is reflected by the receiving diaphragm 51, and returns to the laser interferometer 10 by passing through the same route in reverse.

The distance traveled by the light that is emitted from the laser oscillator and returns to the laser interferometer 10 fluctuates due to the vibration of the receiving diaphragms 51. The changed state becomes clear due to the interference between this returning laser light and the transmitted laser light from the laser oscillator 6.

This data is stored in the data storing apparatus 9, and the data processing and display apparatus 11 processes the stored data, and in the case in which damage 55 is present, it calculates and displays the position and the like.

Next, during the performance of a surface inspection, by which the condition of the surface of the structural member 53 is inspected, the surface inspection ultrasonic wave transmitting portion 19 is used.

In this case, the ultrasonic waves C, which are generated by the transmitting diaphragm 39 of the surface inspection ultrasonic wave transmitting portion 19, are adjusted such that the principal frequency is 10 MHz. In other words, the requirements of the material and the dimensions of the transmitting diaphragm 39, and intensity of the laser light of the laser apparatus 5 are set such that the principal frequency of the generated ultrasonic waves C is 10 MHz.

In this manner, when the principle frequency of the ultrasonic waves C is 10 MHz, the ultrasonic waves C do not penetrate deeply into the structural member 53, but are reflected by the surface. Thus, the condition of the surface can be inspected.

Note that the surface inspection operation is similar to the volumetric inspection operation, and here the redundant explanations thereof have been omitted.

The ultrasonic inspection apparatus 1 is provided with a volumetric inspection ultrasonic wave transmitting portion 17 and a surface inspection ultrasonic wave transmitting portion 19 in which the frequencies of the generated ultrasonic waves are different. Thus, by switching between these portions, inspections having the differing characteristics of a volumetric inspection and a surface inspection, that is, a hybrid inspection, can be carried out with one apparatus.

Thus, in conformity to the type of the structural member 53 and the type of inspection, it is possible to improve the inspection precision and the inspection efficiency and the like by using the ultrasonic inspection apparatus 1 that is provided with an optimal transmitting diaphragm 39.

Thereby, because the laser light that is emitted by the laser apparatus 5 is irradiated to the transmitting diaphragm 39, the transmitting diaphragm 39 generates ultrasonic waves C. These ultrasonic waves C are irradiated to the structural member 53, and thus the deterioration and deformation of the structural member 53 can be prevented.

Thereby, because high output laser light can be handled, the intensity of the generated ultrasonic waves C can be increased. Thus, advantageous inspections can be carried out.

In addition, because adequate inspections can be carried out even if the distance to the structural member 53 is large, the angle of the beam spread can be made large. Thereby, the resolution can be increased, and thus the inspection precision can be increased.

Furthermore, because the optical fibers 23 and 49 are used in the transmission of the laser light, the size of the volumetric inspection ultrasonic wave transmitting portion 17 and the surface inspection ultrasonic wave transmitting portion 19 can reduced, and thus the ultrasonic wave inspection apparatus 1 can be made compact.

In addition, because the ultrasonic waves C are used in the inspection, it is possible to inspect locations through which laser light cannot pass. An example of such a location is one in which sodium, which is a cooling material for fast breeder reactors, is present.

Note that the present invention is not limited by the present embodiment, and it may be suitably modified within a scope that does not depart from the spirit of the present invention.

Figure 6:
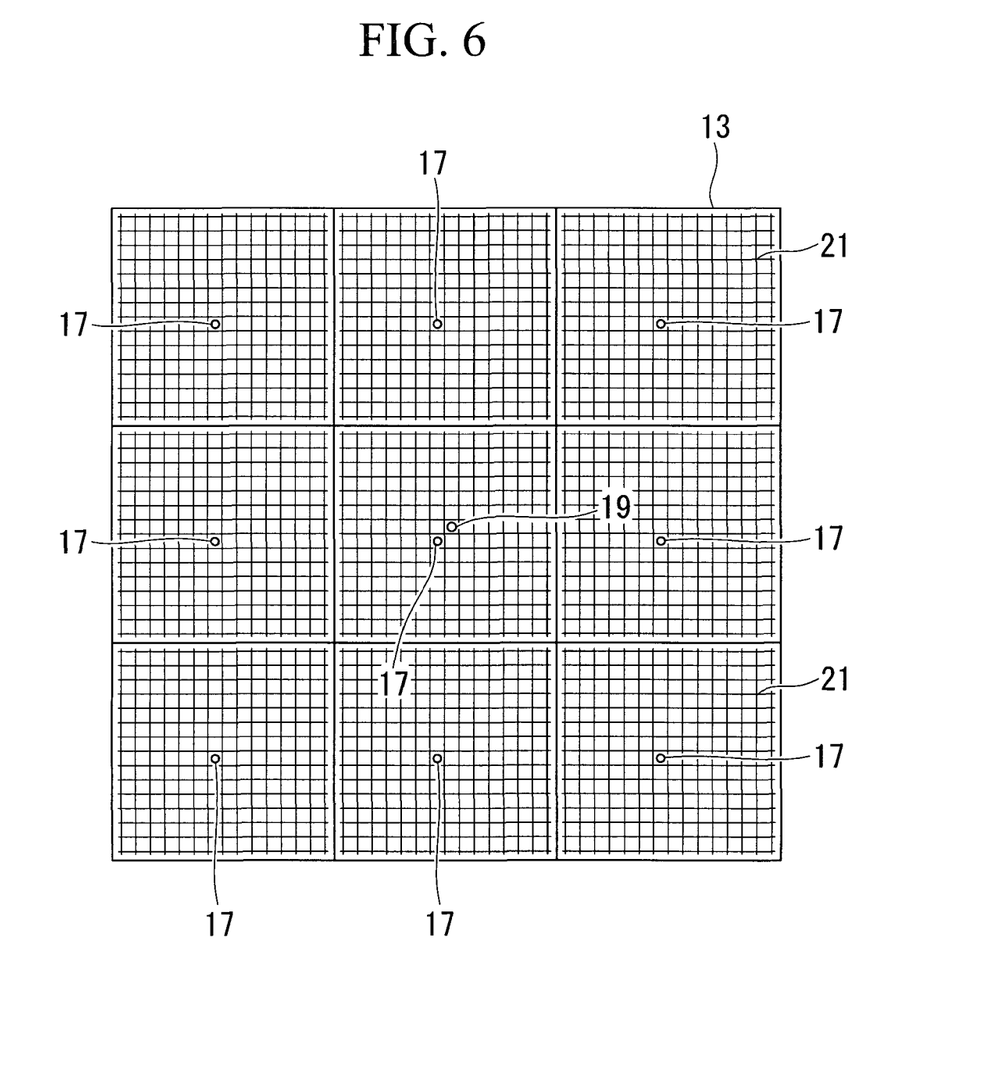
FIG. 6 is a partial frontal view that shows an alternative embodiment of the probe according to an embodiment of the present invention.

For example, the volumetric inspection ultrasonic wave transmitting portion 17, the surface inspection ultrasonic wave transmitting portion 19, and the ultrasonic wave receiving portion 21 may be disposed as shown in FIG. 6.

The main body 13 is, for example, a 200 mm×200 mm substantially rectangular shape, and the surface thereof is divided into nine substantially square shapes. Each volumetric inspection ultrasonic wave transmitting portion 17 is arranged at the substantially central position of each of the divided substantially square parts, and the surface inspection ultrasonic wave transmitting portion 19 is arranged at the substantial center of only the divided substantially square part that is positioned at the center.

The external diameter of the main body 37 of the volumetric inspection ultrasonic wave transmitting portions 17 is set, for example, to about 2 mm. In addition, the external radius of the main body 37 of the surface inspection ultrasonic wave transmitting portion 19 is set, for example, to about 2.5 mm.

The ultrasonic wave receiving portions 21 have an external radius that is set, for example, to about 1 mm, and they are arranged in a 15 row×15 column matrix in each of the divided substantially square parts. In FIG. 6, because the ultrasonic wave receiving portions 21 are comparatively small, only the arrangement positions thereof are shown. That is, the ultrasonic wave receiving portions 21 are arranged at the intersections of the vertical lines and horizontal lines shown in each of the divided substantially square portions in FIG. 6. The vertical lines and horizontal lines do not actually represent any real objects.

Because the divided substantially square portions are disposed in three rows vertically and horizontally, the ultrasonic wave receiving portions 21 are arranged in a 45 column×45 row matrix. Therefore, a total of 2025 ultrasonic wave receiving portions 21 are provided.

When the number is increased in this manner, the inspection efficiency increases, and the inspection precision of the resolution and the like can be improved.

In addition, the volumetric inspection ultrasonic wave transmitting portion 17 and the surface inspection ultrasonic wave transmitting portion 19 do not need to be provided together, and depending on the object, both or only one thereof may be provided.

The invention claimed is:

1. An ultrasonic inspection apparatus comprising:
a laser apparatus that irradiates laser light;
a plurality of ultrasonic wave transmitting portions each having a first diaphragm that is irradiated by the laser light emitted by the laser apparatus and that generates ultrasonic waves;
a plurality of ultrasonic wave receiving portions each having a second diaphragm that vibrates due to receiving the ultrasonic waves that have been reflected from an inspected object and a laser member that emits a laser light to the second diaphragm and receives laser light that has been reflected from the second diaphragm; and
a probe, wherein
the laser apparatus includes an intensity adjusting means, which adjusts a frequency and an intensity of the ultrasonic waves generated by the first diaphragm with adjusting the intensity of the laser light incident to the first diaphragm;
the plurality of the ultrasonic wave transmitting portions are configured so as to generate ultrasonic waves having different frequencies;
the plurality of the ultrasonic wave transmitting portions and the plurality of the ultrasonic wave receiving portions are integrally supported with the probe;
the probe includes a main body which is a box, and a passage portion through which an optical fiber is passed;
the first diaphragm of the plurality of the ultrasonic wave transmitting portions and the second diaphragm of the plurality of the ultrasonic wave receiving portions are arranged so as to face a surface that is opposed to the passage portion of the main body; and
the ultrasonic inspection apparatus carries out inspections by irradiating the ultrasonic waves that are generated by the first diaphragm of the plurality of the ultrasonic wave transmitting portion to the inspected object.

2. The ultrasonic inspection apparatus according to claim 1, wherein the first diaphragm is one that has prescribed frequency characteristics.

3. The ultrasonic inspection apparatus according to claim 1, wherein the first diaphragm is one that has a favorable laser light absorption efficiency.

4. The ultrasonic inspection apparatus according to claim 1, wherein a coating is applied at least to the first diaphragm at the surface to which the laser light is irradiated.

* * * * *